(12) United States Patent  
Planas et al.

(10) Patent No.: US 12,171,925 B2  
(45) Date of Patent: Dec. 24, 2024

(54) SYSTEM AND METHOD WITH CONTAINER VOLUME TRACKING

(71) Applicant: Fenwal, Inc., Lake Zurich, IL (US)

(72) Inventors: Samantha M. Planas, Wauconda, IL (US); Amit J. Patel, Algonquin, IL (US); Jonathan Elicson, Palatine, IL (US); Andrew Vazquez, Chicago, IL (US)

(73) Assignee: Fenwal, Inc., Lake Zurich, IL (US)

( * ) Notice: Subject to any disclaimer, the term of this patent is extended or adjusted under 35 U.S.C. 154(b) by 388 days.

(21) Appl. No.: 17/354,673

(22) Filed: Jun. 22, 2021

(65) Prior Publication Data

US 2021/0402072 A1 Dec. 30, 2021

Related U.S. Application Data

(60) Provisional application No. 63/043,728, filed on Jun. 24, 2020.

(51) Int. Cl.
*A61M 1/34* (2006.01)
*A61M 1/26* (2006.01)
*A61M 1/36* (2006.01)

(52) U.S. Cl.
CPC ............ *A61M 1/341* (2014.02); *A61M 1/262* (2014.02); *A61M 1/3496* (2013.01); *A61M 1/3626* (2013.01)

(58) Field of Classification Search
CPC ............... A61M 1/341; A61M 1/3496; A61M 2205/3331; A61M 2205/3334; A61M 1/3693; A61M 2205/3393; A61M 1/38; A61M 1/3643; A61M 2205/50; A61M 1/3644; A61M 1/3403; A61M 1/3607; A61M 2205/3379; A61M 1/3621; A61M 1/1601

See application file for complete search history.

(56) References Cited

U.S. PATENT DOCUMENTS

2003/0225396 A1* 12/2003 Cartledge ......... A61M 5/14232  
604/890.1  
2003/0233064 A1* 12/2003 Arm .................... A61M 1/3403  
604/4.01  
2007/0161941 A1* 7/2007 Ash ..................... A61M 1/3458  
604/4.01

(Continued)

FOREIGN PATENT DOCUMENTS

WO WO-2018017623 A1 * 1/2018 .............. A61M 1/14

*Primary Examiner* — Adam Marcetich  
(74) *Attorney, Agent, or Firm* — Cook Alex Ltd.

(57) ABSTRACT

A system with container volume tracking includes a pump receiving a line connected to a tracked container, an air sensor to detect air in the line, and a controller coupled to pump and sensor. The controller is configured to monitor pump operation, and determine a volume removed from the container based thereon. If the volume removed is less than a first percentage of a target volume and there is air, continue operation after an air purge. If the volume removed is more than the first percentage and less than a second percentage and if there is air, prompt the user for an input, and continue operation after an air purge if a first input is received or end operation if a second input is received. If the volume removed is more than the second percentage and if there is air, end operation.

8 Claims, 8 Drawing Sheets

(56) References Cited

U.S. PATENT DOCUMENTS

| | | | |
|---|---|---|---|
| 2009/0211989 A1* | 8/2009 | Nguyen | A61M 1/02 |
| | | | 210/767 |
| 2010/0214106 A1* | 8/2010 | Braun | A61M 5/1684 |
| | | | 340/618 |
| 2012/0143115 A1* | 6/2012 | Muller-Spanka | A61M 1/3643 |
| | | | 604/4.01 |
| 2013/0233394 A1* | 9/2013 | Nguyen | A61M 1/3496 |
| | | | 137/395 |
| 2015/0258269 A1* | 9/2015 | Vasta | A61M 1/3627 |
| | | | 210/137 |
| 2016/0058933 A1* | 3/2016 | Ballantyne | G06F 21/565 |
| | | | 210/85 |
| 2016/0089486 A1* | 3/2016 | Patel | A61M 1/36224 |
| | | | 210/96.2 |
| 2016/0089504 A1* | 3/2016 | Patel | A61M 1/3496 |
| | | | 137/1 |
| 2016/0378298 A1* | 12/2016 | Planas | A61M 1/38 |
| | | | 715/771 |
| 2019/0117870 A1* | 4/2019 | Kusters | B01D 63/16 |
| 2019/0160227 A1* | 5/2019 | Li | A61M 39/28 |
| 2020/0360604 A1* | 11/2020 | Kolko | G01G 3/14 |
| 2021/0023283 A1* | 1/2021 | Court | A61M 1/3431 |

\* cited by examiner

SYSTEM AND METHOD WITH CONTAINER VOLUME TRACKING

CROSS-REFERENCE TO RELATED APPLICATION

This application claims the benefit of and priority to U.S. Provisional Patent Application Ser. No. 63/043,728, filed on Jun. 24, 2020, the disclosure of which is incorporated herein by reference in its entirety.

TECHNICAL FIELD

The present disclosure is generally directed to a biological fluid processing system. More particularly, the present disclosure is directed to a biological fluid processing system with a system and method for tracking fluid volume in a container.

BACKGROUND

As part of a biological fluid processing system or method, for example a blood processing system or method, certain components of the biological fluid may be separated and retained, while other components of the biological fluid are separated and returned to the source (e.g., a donor or a container). The procedure may be performed using reusable equipment, including drives, pumps, and clamps controlled by a controller, paired with a disposable set, including tubing and containers. The containers also may contain other fluids that may be returned to the source in addition to the components that are separated and returned.

For example, plasmapheresis is an apheresis procedure in which whole blood is withdrawn from a source, such as a donor, the plasma is separated from the cellular blood components (red blood cells, platelets and leukocytes) and retained, and the cellular blood components are returned to the donor. The system for performing plasmapheresis may include reusable equipment, such as pumps to move fluids into and out of containers, a drive for a separator such as a spinning membrane separator, and clamps, associated with a disposable plasmapheresis set. In addition to the cellular blood components, saline may be infused to the source at the end of a plasmapheresis procedure.

One problem that has arisen with such a plasmapheresis system is obtaining an accurate determination of the volume remaining in the saline solution container during the saline infusion. Conventionally, the saline container is placed on a solution pole that does not have a built-in weigh scale. Consequently, it is not possible for the system controller to use the weight of the fluid in the container to determine the volume of fluid in the container.

The saline solution from the container is conventionally reinfused to the source using a pump, such as a rotary peristaltic pump. One solution to the problem of determining the remaining saline volume in the saline container has involved, in part, tracking the number of pump revolutions. From the number of pump revolutions, the system controller may estimate the volume pumped from the container. Unfortunately, this estimate may involve a high degree of error. The solution also may involve monitoring pressure to determine if the container is empty (e.g., a negative pressure may indicate that a flexible container has collapsed), but this also is susceptible to error if the saline container is not very flexible or if a filter is used on the disposable set.

It would be desirable to provide a system that overcame, at least in part, the disadvantages of conventional systems that determine the fluid volume remaining in a container, such as a saline container used in a plasmapheresis procedure.

SUMMARY

In an aspect, a system with container volume tracking includes a pump configured to receive a line connected to a tracked container and an air sensor associated with the line and configured to detect if air is in the line. The system also includes an output display configured to display prompts to a user and an input device to receive inputs from the user. Further, the system includes a controller coupled to the pump, the air sensor, the output display, and the input device.

The controller is configured to monitor operation of the pump, and determine a volume removed from the tracked container based on the operation of the pump. According to a (first) mode, if the volume removed from the tracked container is less than a first percentage of a target volume from the tracked container and if the air sensor detects air in the line, the controller is configured to continue operation of the pump after an air purge. If the volume removed from the tracked container is more than the first percentage of the target volume from the tracked container and less than a second percentage of the target volume from the tracked container and if the air sensor detects air in the line, the controller is configured to prompt the user for an input. In addition, the controller is configured to continue the operation of the pump after an air purge if a first input is received, and to end the operation of the pump if a second input is received. If the volume removed from the tracked container is more than the second percentage of the target volume from the tracked container and if the air sensor detects air in the line, the controller is configured to end the operation of the pump.

In another aspect, a method with container volume tracking includes monitoring operation of a pump configured to receive a line connected to a tracked container, and determining a volume removed from the tracked container based on the operation of the pump. According to a (first) mode, if the volume removed from the tracked container is less than a first percentage of a target volume from the tracked container and if an air sensor associated with the line detects air in the line, the method includes continuing operation of the pump after an air purge. If the volume removed from the tracked container is more than the first percentage of the target volume from the tracked container and less than a second percentage of the target volume from the tracked container and if the air sensor detects air in the line, the method includes prompting the user for an input. In addition, the method includes continuing the operation of the pump after an air purge if a first input is received, and ending the operation of the pump if a second input is received. If the volume removed from the tracked container is more than the second percentage of the target volume from the tracked container and if the air sensor detects air in the line, the method includes ending the operation of the pump.

DETAILED DESCRIPTION

A more detailed description of the systems and methods in accordance with the present disclosure is set forth below. It should be understood that the description below of specific devices and methods is intended to be exemplary, and not exhaustive of all possible variations or applications. Thus, the scope of the disclosure is not intended to be limiting, and should be understood to encompass variations or embodiments that would occur to persons of ordinary skill.

Initially, a system with container volume tracking, according to the disclosure embodiments, includes a pump configured to receive a line connected to a tracked container and an air sensor associated with the line and configured to detect if air is in the line. The system also includes an output display configured to display prompts to a user and an input device to receive inputs from the user. Further, the system includes a controller coupled to the pump, the air sensor, the output display, and the input device.

The controller is configured to monitor operation of the pump, and determine a volume removed from the tracked container based on the operation of the pump.

If the volume removed from the tracked container is less than a first percentage of a target volume from the tracked container and if the air sensor detects air in the line, the controller is configured to continue operation of the pump after an air purge.

If the volume removed from the tracked container is more than the first percentage of the target volume from the tracked container and less than a second percentage of the target volume from the tracked container and if the air sensor detects air in the line, the controller is configured to prompt the user for an input. In addition, the controller is configured to continue the operation of the pump after an air purge if a first input is received, or end the operation of the pump if a second input is received.

If the volume removed from the tracked container is more than the second percentage of the target volume from the tracked container and if the air sensor detects air in the line, the controller is configured to end the operation of the pump.

While the afore-mentioned container volume tracking system may be used in other settings, the container volume tracking system is described herein as incorporated into an embodiment of an automated plasmapheresis system. In particular, the container volume tracking system is described herein as incorporated into the plasmapheresis system to track the container volume of a saline solution container where a scale is not available for use in determining volume removed from the saline solution container. As such, the structure and operation of the automated plasmapheresis system is explained first as many of the components of the container volume tracking system also perform other functions within the automated plasmapheresis system and the two systems work in concert with each other.

Figure 1:
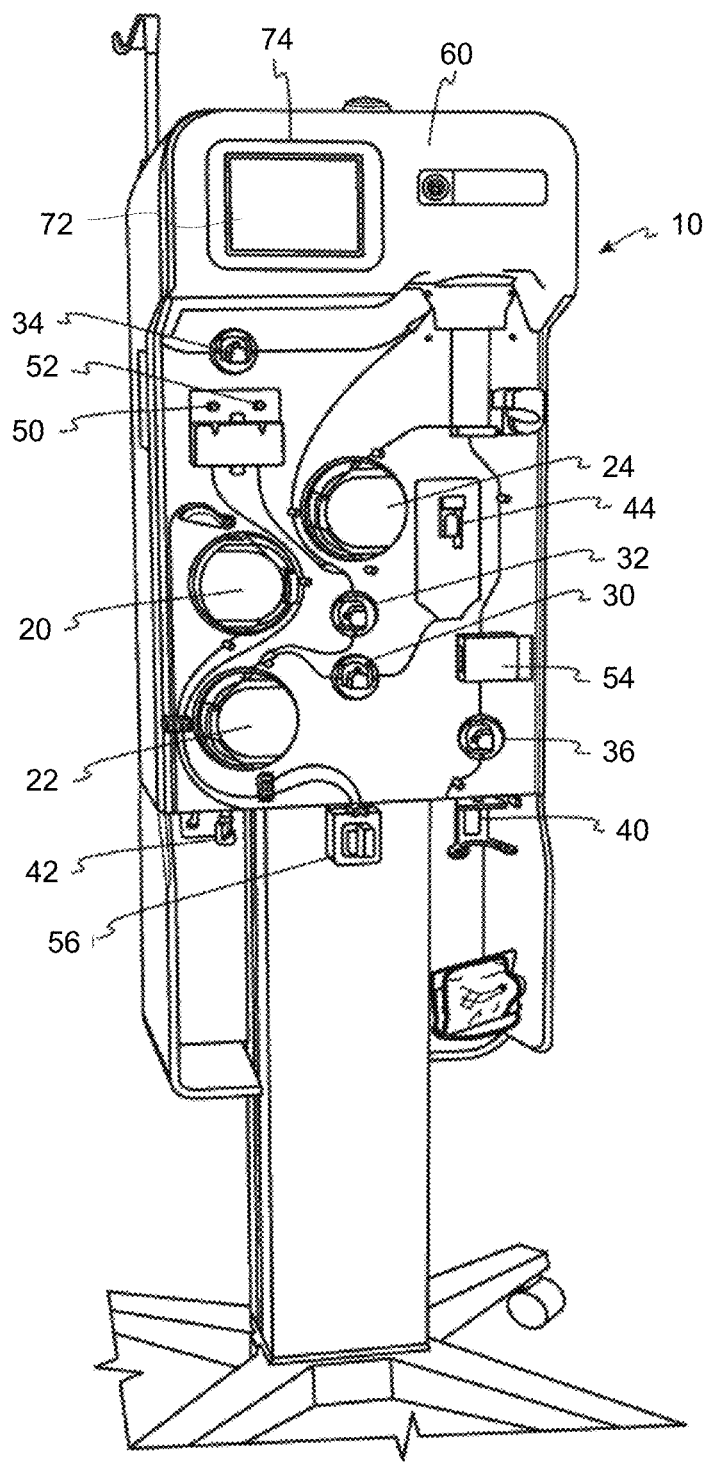
FIG. 1 is a perspective view of a hardware component of an embodiment of a plasmapheresis system incorporating a container volume tracking system.
Figure 2:
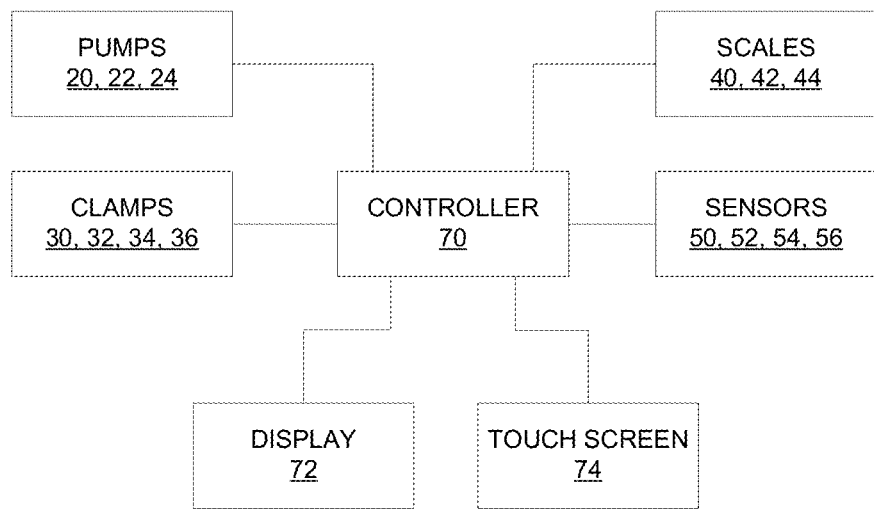
FIG. 2 is a schematic view of a controller of the hardware component of FIG. 1.
Figure 3:
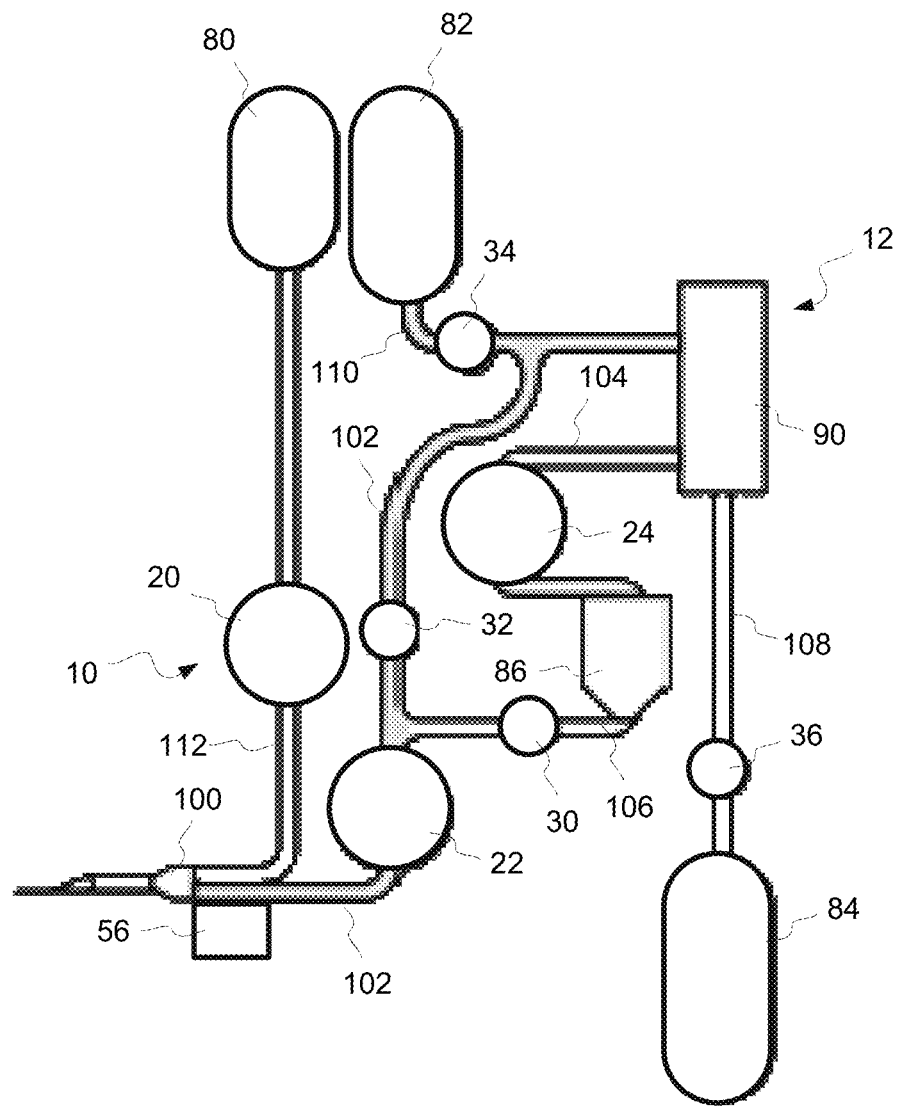
FIG. 3 is a schematic view of a disposable set usable with the hardware component of FIG. 1, illustrating the disposable set interfacing with the hardware component.
Figure 4:
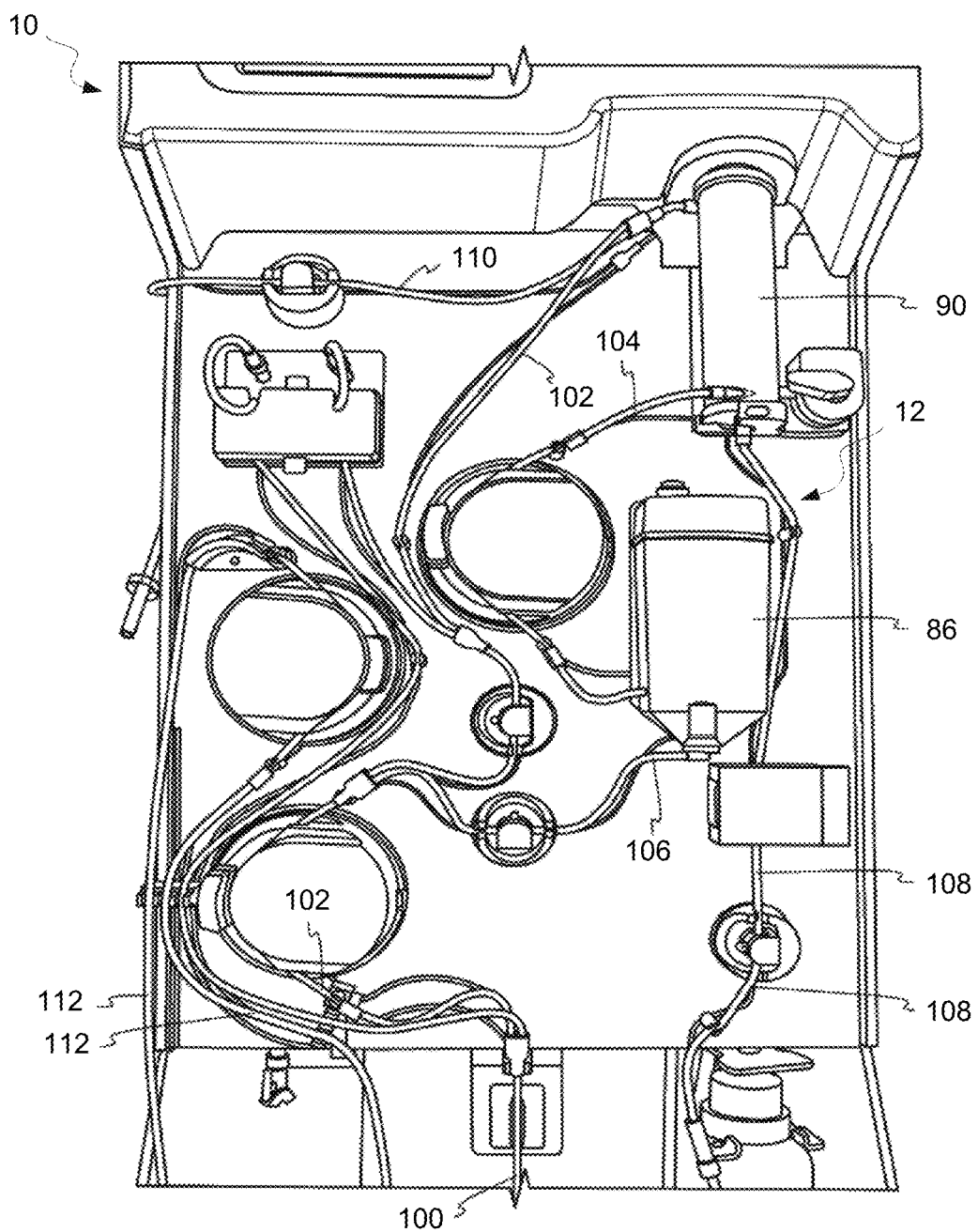
FIG. 4 is a perspective view of a front panel of a housing of the hardware component of FIG. 1 illustrating the disposable set interfacing with the hardware component.
Figure 5:
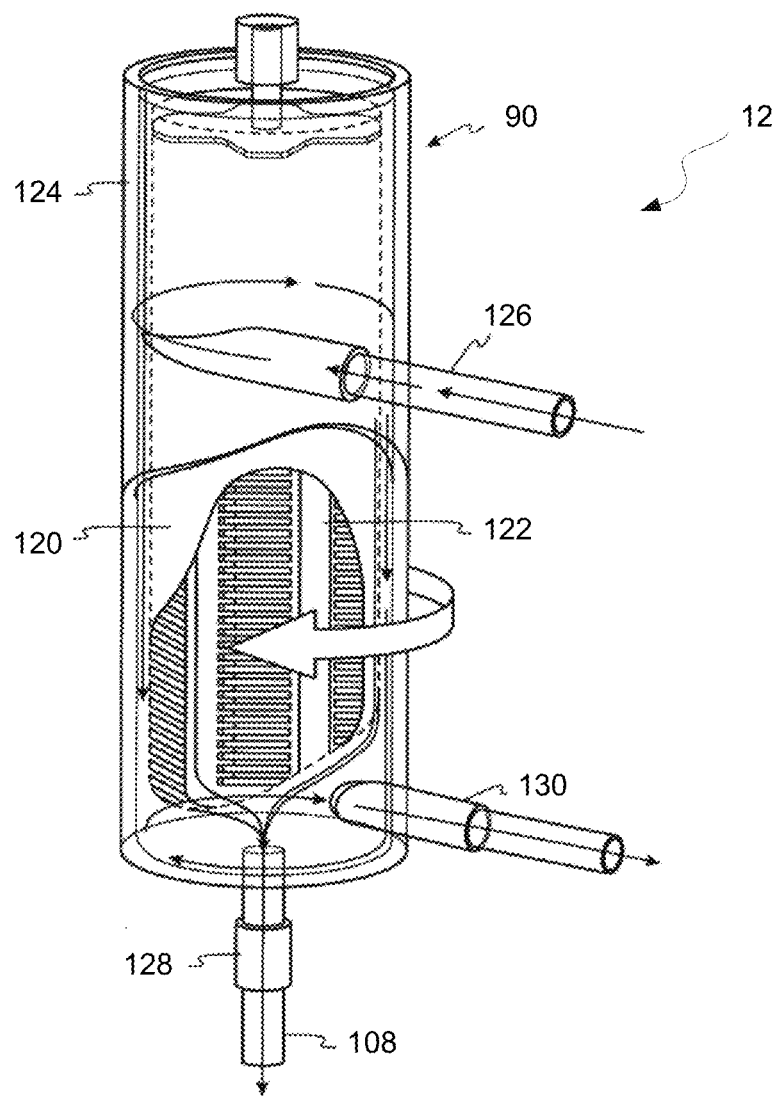
FIG. 5 is a perspective view of a spinning membrane separator of the hardware component of FIG. 1, with portions of the spinning membrane separator broken away to show detail.

With reference to FIGS. 1-5, the embodiment of the automated plasmapheresis system incorporating the container volume tracking system includes a hardware component, generally designated 10 in FIGS. 1-4, and a disposable set, generally designated 12 in FIGS. 3-5.

The hardware component 10 includes pumps, drives, clamps (or valves, e.g., pinch valves), scales, and sensors, mounted on a housing in which is disposed a programmable controller that is coupled to the pumps, drives, clamps, scales, and sensors and configured (e.g., programmed) to operate the elements to process and move a biological fluid (e.g., blood), its components (e.g., red blood cells, plasma), and other solutions through the disposable set 12. The disposable set 12 may include an integrally connected separator, containers, and tubing (or lines) to transport the biological fluid and solutions within a sterile fluid pathway.

Turning first to FIG. 1, the hardware component 10 includes three pumps 20, 22, 24. According to the illustrated embodiment, the pumps 20, 22, 24 are peristaltic pumps, in particular rotary peristaltic pumps. The pumps may be referred to as an anticoagulant (AC) pump 20, a blood pump 22, and a cell pump 24, and the operation of the pumps 20, 22, 24 is discussed below. The hardware component may also include a drive for use with the integrally connected separator that is part of the disposable set 12.

The hardware component 10 additionally includes four clamps 30, 32, 34, 36 into which the disposable set 12 is installed. The clamps may be referred to as a reinfusion clamp 30, a blood clamp 32, a saline clamp 34, and a plasma clamp 36. As was the case with the pumps, the specific operation of the clamps is discussed below.

The hardware component 10 further includes three weigh scales 40, 42, 44 to monitor a current plasma collection volume, an AC solution volume, and a concentrated cellular content volume, respectively. The system also includes various sensors and detectors, including a venous pressure sensor 50, a separator pressure sensor 52, optical blood detectors 54, and an air detector 56.

As illustrated in FIG. 1, the pumps 20, 22, 24, the clamps 30, 32, 34, 36, the scales 40, 42, 44, and the sensors 50, 52, 54, 56 may be mounted on a front panel of a housing 60. Parts of the pumps 20, 22, 24, the clamps 30, 32, 34, 36, the scales 40, 42, 44, and the sensors 50, 52, 54, 56 may be disposed outside the housing to interface with the disposable set 12, and other parts may be disposed within the housing 60.

As illustrated in FIG. 2, the hardware component 10 also may include a programmable controller 70, which controller 70 is configured to control operation of the system, for example using a method of operation as is explained below to perform a plasmapheresis procedure with container volume tracking. The programmable controller 70 may be disposed in the housing 60.

The controller 70 may include a microprocessor (which, in fact may include multiple physical and/or virtual processors). According to other embodiments, the controller may include one or more electrical circuits designed to carry out the actions described herein. In fact, the controller 70 may include a microprocessor and other circuits or circuitry. In addition, the controller 70 may include one or more memories. The instructions by which the microprocessor is programmed may be stored on the one or more memories associated with the microprocessor, which memory/memories may include one or more tangible non-transitory computer readable memories, having computer executable instructions stored thereon, which when executed by the microprocessor, may cause the microprocessor to carry out one or more actions as described below.

The controller 70 may be coupled (i.e., directly or indirectly connected) to the equipment of the reusable hardware 10, such as pumps 20, 22, 24, the drive, the clamps 30, 32, 34, 36, the scales 40, 42, 44, and the sensors 50, 52, 54, 56. The controller 70 may operate these devices or receive input/signals from these devices, each of which may be an assembly of other devices or equipment, to selectively cause the fluid to flow through the disposable set 12, for example to selectively cause fluid to flow from the source and through the separator, where it is separated into at least two components, one of which may be returned to the source. The controller 70 also may operate certain of these devices to carry out a container volume tracking method as explained below.

The hardware component 10 may also include an output device, for example in the form of a display 72 (such as an electronic display) and an input device, for example in the form of a touch screen 74 associated with the display 72. The display 72 and touch screen 74 may provide a graphical user interface ("GUI") through which an operator can program the controller 70 to perform a plasmapheresis procedure. The display 72 with touch screen 74 also may be used as part of the container volume tracking system.

As illustrated in FIGS. 3 and 4, the disposable set 12 interfaces with the hardware component 10 to process a biological fluid (e.g., blood). As mentioned above, the set 12 may include one or more containers 80, 82, 84, 86, a separator 90 (which may be attached to and cooperate with the drive of the hardware component 10), and one or more needles 100 to connect to the source. The set 12 may also include a plurality of lines (defined by tubing) 102, 104, 106, 108, 110, 112. FIG. 4 illustrates the details of the cooperation of the lines 102, 104, 106, 108, 110, 112 with the hardware component 10.

As seen in FIG. 3, the first container 80 contains anticoagulant solution, while the second container 82 contains saline solution. The container 80 is attached to the scale 42, while the saline solution container 82 is hung from a solution pole (top left corner of FIG. 1) without a scale associated therewith. The third container 84 is used for collection of a first component from the separator 90, i.e., plasma, and the fourth container 86 is used for collection of a second component from the separator 90, i.e., concentrated cells. Thus, the container 86 may be referred to as the concentrated cell reservoir. The container 84 is attached to the scale 40, while the container 86 is attached to the scale 44.

The lines 102, 104, 106, 108, 112 exist to introduce whole blood from the source into the system during collection and to return concentrated cells to the source during reinfusion, while line 110 is used for the priming with or the infusion of other solutions. To this end, line 102 (also referred to as the blood line) is used to transport anticoagulated whole blood to the separator 90. The line 104 (also referred to as the cell line) is used to transport concentrated cells to the reservoir 86 and then line 106 (also referred to as the reinfusion line) is used to transport concentrated cells from the reservoir 86 to the needle 100. The line 108 (also referred to as the plasma line) is used to transport plasma to the plasma collection container 84. Lines 110 and 112 (referred to as the saline line and the AC line, respectively) are used to transport saline solution from the container 82, and anticoagulant solution from the AC container 80.

As illustrated in FIGS. 3 and 4, these lines 102, 104, 106, 108, 110, 112 interface with the pumps 20, 22, 24 and the clamps 30, 32, 34, 36.

In particular, the AC pump 20 interfaces with the line 112 to deliver anticoagulant solution at a controlled rate as whole blood enters the set from the source (e.g., a donor or a container). The blood pump 22 interfaces with the line 102 to deliver anticoagulated whole blood to the separator 90 during the collection phase of the procedure and to return concentrated cellular components and, if desired, replacement fluid to the source during the reinfusion phase of the procedure. The cell pump 24 interfaces with line 104 to deliver concentrated cellular components from the separator 90 to the reservoir 86 during the collection phase.

The reinfusion clamp 30 closes to block the reinfusion line 106 during the delivery of the anticoagulated whole blood to the separator 90, and is open during the reinfusion phase to allow the blood pump 22 to reinfuse the concentrated cellular components from the reservoir 86 to the source. The blood clamp 32 opens during the collection phase to allow anticoagulated whole blood to be pumped to the separator 90 and closes during the reinfusion phase to block the blood line above the clamp 32. The saline clamp 34 closes to block the saline line 110 during the collection phase and during reinfusion of the separated cellular components. If saline is to be used as a replacement fluid, the blood clamp 32 and the saline clamp 34 open to permit saline to be returned to the source. The plasma clamp 36 opens during the collection phase to allow plasma to flow into the plasma collection container 84 and closes during the reinfusion phase.

During a plasmapheresis procedure, the hardware 10 may be operated to perform one or more cycles, each cycle having a collection/separation phase followed by a return or reinfusion phase. Typically, a plasmapheresis procedure performed with a single venipuncture needle 100 involves multiple cycles of collection/separation and reinfusion.

During the collection phase, anticoagulant solution is pumped at a controlled rate and mixed with whole blood as it enters the disposable set 12. The anticoagulated blood is pumped to the separator 90, where plasma is separated from the cellular components and directed to the plasma collection container 84. The cellular components are pumped from the separator 90 to the reservoir 86.

At this point, the structure and operation of the separator 90 is now described with reference to FIG. 5.

The separator 90 has a spinning membrane 120 mounted to a rotor 122 for rotation within a case 124 to separate blood into components. A detailed description of a spinning membrane separator may be found in U.S. Pat. No. 5,194,145, which patent is incorporated herein by reference in its entirety. As can be appreciated, in a different system, separation of the whole blood may be accomplished by centrifugation. See, e.g., U.S. Pat. No. 5,360,542, which patent is also incorporated herein by reference in its entirety.

The anticoagulated whole blood enters the separator 90 through a whole blood input port 126. The plasma is separated by the spinning membrane and then passes out of a plasma output port 128, through a plasma line 108, and into the plasma collection container 84. Concentrated cells are pumped out of a concentrated cell output port 130 into a reservoir 86, where the cells remain until return to the source.

The collection phase stops when the reservoir 86 reaches a target volume of concentrated cells or if the target plasma collection volume has been achieved.

During the reinfusion phase, the blood pump 32 reverses direction and pumps the concentrated cells from the reservoir 86 back to the source through the needle 100. If a saline infusion (or protocol) is selected, wherein saline solution is returned to the source as a replacement fluid for the collected plasma, the final reinfusion phase is followed by the saline infusion. It is also possible for tracked saline infusion to occur in part during the plasmapheresis procedure, however. For example, an intra-procedure saline infusion (of IP saline protocol) may occur after a portion of the plasma is collected, with the remainder infused after the final reinfusion phase is complete. It is further possible for saline infusion to occur in an untracked fashion during the procedure, as will be explained below.

Figure 6:
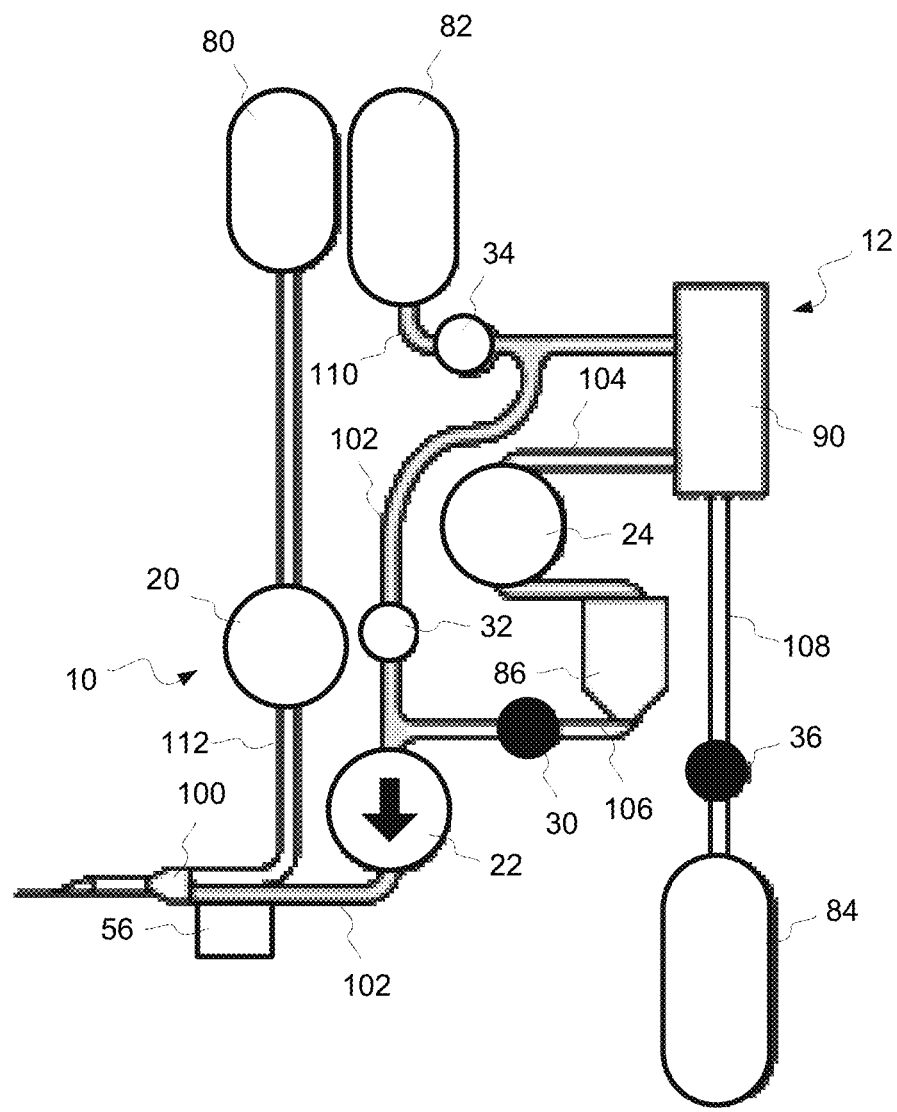
FIG. 6 is a schematic view illustrating operation of the plasmapheresis system of FIG. 1 in a saline infusion phase.

As mentioned previously, the embodiment of the automated plasmapheresis system illustrated in FIGS. 1-5 has incorporated therein a container volume tracking system, in particular for tracking the volume removed from the saline solution container 82 during the saline infusion. While the term volume removed is used herein, it will be recognized that this could alternatively be phrased in terms of volume remaining, considering the direct relationship between these two concepts and the target volume to be infused (which volume likewise may be directly related to the total volume of the tracked container). During the saline infusion, the system 10, 12 may be configured as represented schematically in FIG. 6, with only pump 22 operating, clamps 32, 34 open and clamps 30, 36 closed. As mentioned above, the container volume tracking system includes one or more elements of the hardware 10 that are used to perform the plasmapheresis procedure, and that are also used to perform the container volume tracking method.

In particular, the embodiment of the container volume tracking system includes the blood pump 22 configured to receive the line 102 connected to the tracked container, the saline container 82. In particular, the line 102 is connected to the saline line 110 and saline line 110 is connected directly to the saline container 82. The system also includes the air sensor 56 associated with the line 102 and configured to detect if air is in the line 102. The system further includes the output display 72 configured to display prompts to a user, and the input device/touch screen 74 to receive inputs from the user. Further, the system includes the controller 70 coupled to the pump 22, the air sensor 56, the output display 72, and the input device 74.

The system tracks the volume removed from the container 82 to determine when the saline infusion is complete. This container volume tracking uses two types of information: operational information concerning the pump 22 and whether air is detected by the air sensor 56. The operational information concerning the pump 22 may vary, but according to one embodiment wherein the pump 22 is a rotary peristaltic pump, the container volume tracking system monitors the operation of the pump by tracking the revolutions of the pump 22. The operational information concerning the pump 22 is used to determine the approximate volume removed from the container 82, and this volume information may be compared with one or two different volume thresholds (depending on mode, as explained below) in conjunction with whether the air sensor 56 detects air in the line 102. The container volume tracking method is illustrated in detail in FIGS. 7 and 8.

Figure 7:
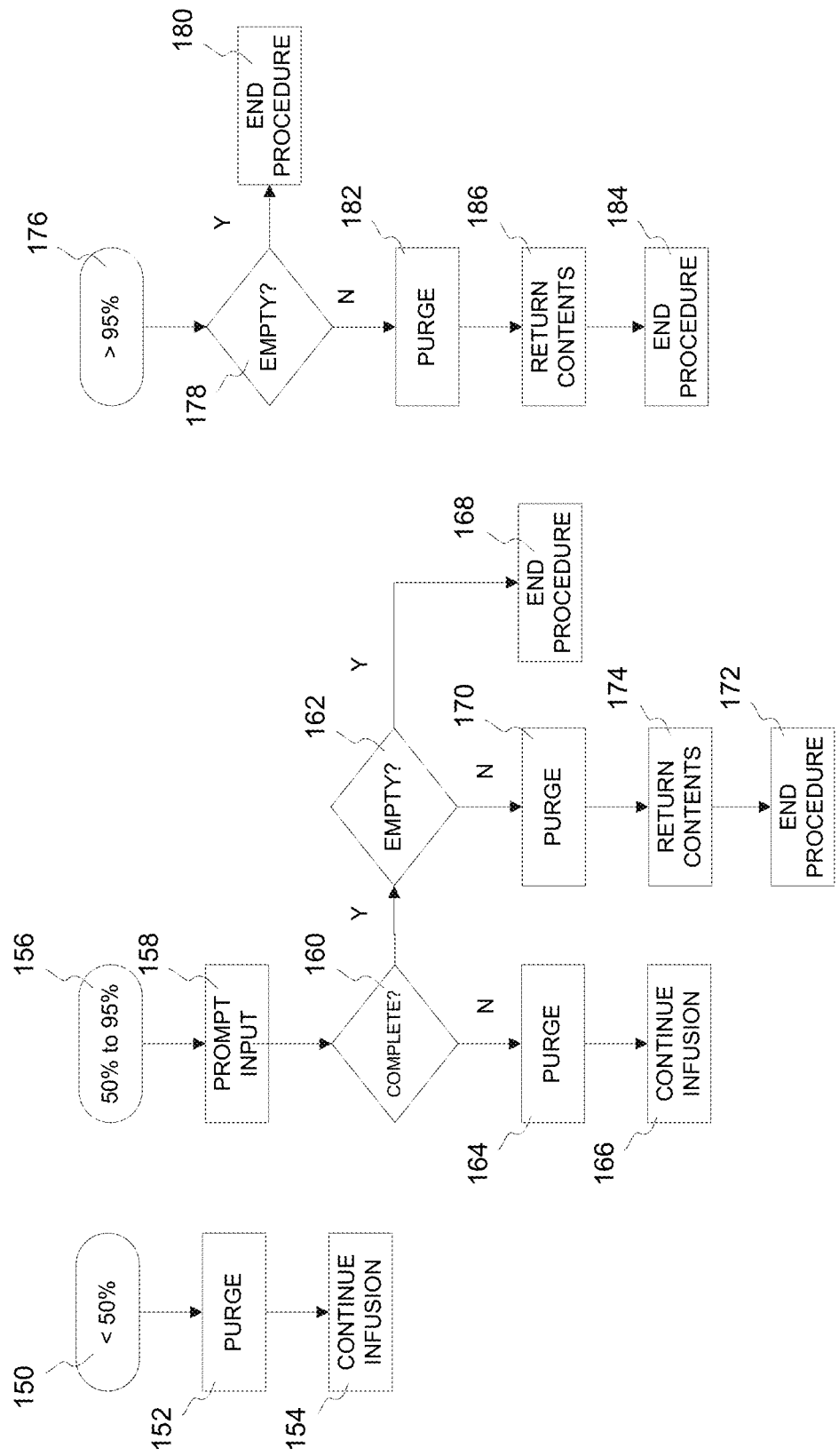
FIGS. 7 and 8 are a block diagrams of an embodiment of a container volume tracking method.
Figure 8:
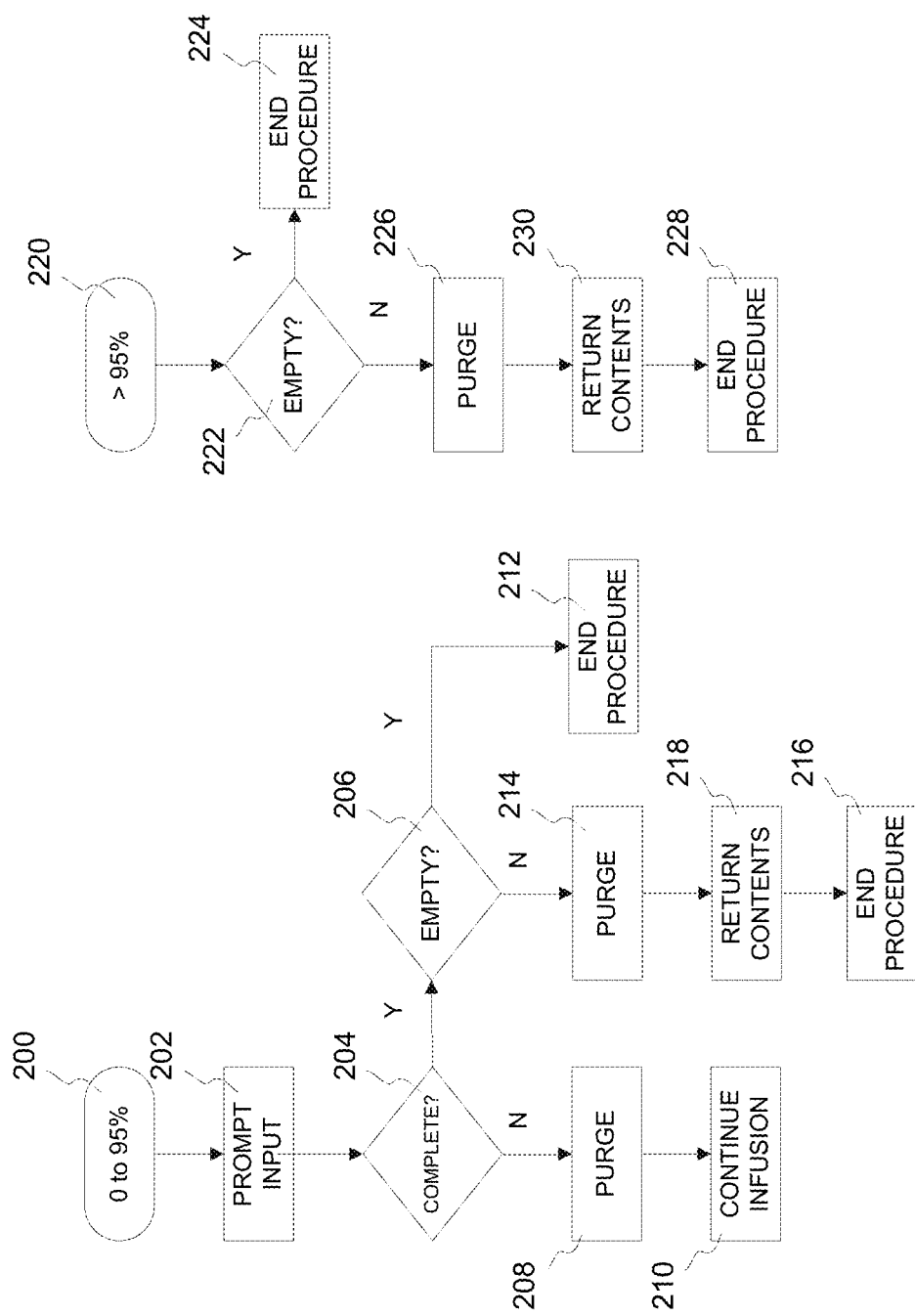

According to the illustrated embodiment, the container volume tracking method selects between the two different modes depending on whether the saline infusion at the end of the plasmapheresis procedure was preceded by an untracked, gravity-driven saline infusion occurring during the plasmapheresis procedure. If the saline infusion was not preceded by an untracked gravity-driven saline infusion occurring during the plasmapheresis procedure, the (first) mode of FIG. 7 is used. If the saline infusion was preceded by a saline infusion occurring during the plasmapheresis procedure, the (second) mode of FIG. 8 is used. It is possible, according other embodiments, for the container volume tracking system to operate only according to the mode of FIG. 7 or FIG. 8, for example.

According to the first mode, the method establishes three volume ranges defined by two different volume thresholds. For example, the two volume thresholds may be 50% and 95% of the target volume from the tracked container, such that the three volume ranges include (i) less than 50% of the target volume from the tracked container, (ii) more than 50% of the target volume from the tracked container and less than 95% of the target volume from the tracked container, and (iii) more than 95% of the target volume from the tracked container. According to the illustrated embodiment, either the first or second range may include 50%, and either the second or third range may include 95%; one range will necessarily not include the value of either 50% or 95% if it is included in other.

According to the illustrated embodiment, in the first mode, if the controller 70 monitors the operation of the pump 22 and determines that the volume removed from the tracked container 82 based on the operation of the pump 22 is within the first range, then the controller 70 determines if the sensor 56 detects air in the line 102 (block 150). If air is detected, then the controller 70 waits for an air purge (block 152), after which the controller 70 continues operation of the pump 22 (block 154). Optionally, if the air is detected and an input is received to end the procedure, then the controller 70 ends the operation of the pump 22 instead.

Thus, in the first range, (at or) below 50% of the target volume from the container, the controller 70 assumes that the container 82 is not empty. Consequently, air detected in the line 102 by the sensor 56 suggests that air needs to be purged from the line 102, and then operation can continue. It is possible that the operator may wish to terminate operation of the saline infusion instead, and the system may also provide for this option.

Again in the first mode, if the controller 70 monitors the operation of the pump 22 and determines that the volume removed from the tracked container 82 based on the operation of the pump 22 is within the second range, then the controller 70 determines if the sensor 56 detects air in the line 102 (block 156). If air is detected, then the controller 70 controls the display 72 to prompt the user for an input (block 158) and determines if an input is received (block 160). A first input causes the controller 70 to await an air purge (block 164), after which the controller 70 continues operation of the pump (block 166), while a second input results in termination of the saline infusion (end operation of the pump 22). This may occur directly (block 168), or the controller 70 may await an air purge (block 170) and then end operation of the pump 22 (block 172), potentially with a return contents from the reservoir 86 (block 174). The difference occurs based on an automated determination if the reservoir 86 is empty (block 162), which may rely on sensor input to the controller 70.

Thus, in the second range, (at or) above 50% of the target volume from the container to (at or) below 95% of the target volume from the container, the controller 70 does not assume that the container 82 is either empty or not empty. Consequently, air detected in the line 102 by the sensor 56 may suggest that air needs to be purged from the line 102 or may suggest that the container is empty. The prompt permits the operator to continue or terminate. Furthermore, termination may or may not require an additional purge and return of contents.

Finally in the first mode, if the controller 70 monitors the operation of the pump 22 and determines that the volume removed from the tracked container 82 based on the operation of the pump is in the third range, then the controller 70 determines if the air sensor 56 detects air in the line 102 (block 176). If air is detected, then the controller 70 determines whether to consider the reservoir 86 empty based on sensor input to the controller 70 (block 178). A positive determination results in termination of the saline infusion (end operation of the pump 22) (block 180), while a negative determination causes the controller 70 to await an air purge (block 182) and then to end operation of the pump 22 (block 184), potentially with a return of contents from the reservoir 86 (block 186).

In the third range, at or above 95% of the target volume from the tracked container, the controller 70 assumes that air detected in the line 102 means that the container 82 is empty. This is a reasonable assumption as the determination of the volume using the operation of the pump 22, such as by tracking the revolutions of the pump 22, may vary by 5%, for example. Thus, the controller 70 ends operation of the pump 22, optionally with an air purge and return of contents.

According to the second mode, the method establishes two volume ranges defined by a single volume threshold. For example, the volume threshold may be 95% of the target volume from the tracked container, such that the two volume ranges include (i) less than 95% (or, 0 to 95%) of the target volume from the tracked container, and (ii) more than 95% of the target volume from the tracked container. According to the illustrated embodiment, either the first or second range may include 95%, and the other will necessarily not include the 95%.

In the second mode, if the controller 70 monitors the operation of the pump 22 and determines that the volume removed from the tracked container 82 based on the operation of the pump 22 is within the first range, then the controller 70 detects if the sensor 56 detects air in the line 102 (block 200). If air is detected, then the controller 70 controls the display 70 to prompt the user for an input (block 202) and determines if an input is received (block 204). A first input causes the controller 70 to await an air purge (block 208), after which the controller 70 continues operation of the pump (block 210), while a second input results in termination of the saline infusion (end operation of the pump 22). This termination may occur directly (block 212), or the controller 70 may await an air purge (block 214) and then end operation of the pump 22 (block 216), potentially with a return contents from the reservoir 86 (block 218). The difference occurs based on an automated determination if the reservoir 86 is empty (block 206), which may rely on sensor input to the controller 70.

In addition, in the second mode, if the controller 70 monitors the operation of the pump 22 and determines that the volume removed from the tracked container 82 based on the operation of the pump is in the second range, then the controller 70 determines if the air sensor 56 detects air in the line 102 (block 220). If air is detected, then the controller 70 determines whether to consider reservoir 86 empty based on sensor input to the controller 70 (block 222). A positive determination results in termination of the saline infusion (end operation of the pump 22) (block 224), while a negative determination causes the controller 70 to await an air purge (block 226) and then to end operation of the pump 22 (block 228), potentially with a return contents from the reservoir 86 (block 230).

It will be recognized that the second mode, which is selected based on a prior untracked infusion of saline, does not have a range over which the controller 70 assumes the container 82 is not empty. Instead, because of the potential uncertainties caused by the earlier infusion being untracked, the second mode requires input from the user or operator over a wider range of conditions. The second mode may operate very similarly to the first mode other than the number of thresholds and number of ranges defined.

Thus, an improved system has been disclosed. The description provided above, and the other aspects provided below, are intended for illustrative purposes, and are not intended to limit the scope of the disclosure to any particular method, system, apparatus or device described herein.

Other Aspects

Aspect 1. A system with container volume tracking, comprising:
 a pump configured to receive a line connected to a tracked container;
 an air sensor associated with the line and configured to detect if air is in the line;
 an output display configured to display prompts to a user;
 an input device to receive inputs from the user; and
 a controller coupled to the pump, the air sensor, the output display, and the input device, the controller configured to:
  monitor operation of the pump;
  determine a volume removed from the tracked container based on the operation of the pump; and
  according to a first mode:
   if the volume removed from the tracked container is less than a first percentage of a target volume from the tracked container and if the air sensor detects air in the line, continue operation of the pump after an air purge;
   if the volume removed from the tracked container is more than the first percentage of the target volume from the tracked container and less than a second percentage of the target volume from the tracked container and if the air sensor detects air in the line, prompt the user for an input, and continue operation of the pump after an air purge if a first input is received or end the operation of the pump if a second input is received; and
   if the volume removed from the tracked container is more than the second percentage of the target volume from the tracked container and if the air sensor detects air in the line, end the operation of the pump.

Aspect 2. The system according to aspect 1, wherein the controller is configured to, according to a second mode:
 if the volume removed from the tracked container is less than the second percentage of the target volume from the tracked container and if the air sensor detects air in the line, prompt the user for an input, and continue operation of the pump after an air purge if a first input is received or end the operation of the pump if a second input is received; and
 if the volume removed from the tracked container is more than the second percentage of the target volume from the tracked container and if the air sensor detects air in the line, end the operation of the pump.

Aspect 3. The system according to aspect 2, wherein the controller is configured to select the first mode or the second mode based on an untracked infusion from the tracked container.

Aspect 4. The system according to any one of aspects 1-3, wherein the first percentage is 50% and the second percentage is 95%.

Aspect 5. The system according to any one of aspects 1-4, wherein the pump is a rotary peristaltic pump, and the controller is configured to monitor the operation of the pump by tracking revolutions of the pump.

Aspect 6. The system according to any one of aspects 1-5, further comprising:
- a separator having an input port, a first output port, and a second output port, the separator configured to separate a biological fluid that enters at the input port into a first component that exists at the first output port and a second component that exists at the second output port,
- the controller coupled to the separator, the controller configured to selectively operate the separator and to selectively operate the pump to deliver biological fluid to the separator and to draw fluid from the tracked container.

Aspect 7. The system according to aspects 6, further comprising:
- a scale to receive a first component container, the first component container in fluid communication with the first output port,
- the controller coupled to the scale, the controlled configured to monitor the scale to determine when a target volume of the first component is received in the first component container, to operate the pump to deliver to the biological fluid to the separator and to operate the separator until the target volume is received in the first component container, and to operate the pump to deliver fluid from the tracked container after the target volume is received in the first component container.

Aspect 8. The system according to any one of aspects 1-7, wherein the separator comprises a spinning membrane.

Aspect 9. A method with container volume tracking, the method comprising:
- monitoring operation of a pump configured to receive a line connected to a tracked container;
- determining a volume removed from the tracked container based on the operation of the pump; and
- according to a first mode:
  - if the volume removed from the tracked container is less than a first percentage of a target volume from the tracked container and if an air sensor associated with the line detects air in the line, continuing operation of the pump after an air purge;
  - if the volume removed from the tracked container is more than the first percentage of the target volume from the tracked container and less than a second percentage of the target volume from the tracked container and
  - if the air sensor detects air in the line, prompting the user for an input, and continuing operation of the pump after an air purge if a first input is received or ending the operation of the pump if a second input is received; and
  - if the volume removed from the tracked container is more than the second percentage of the target volume from the tracked container and if the air sensor detects air in the line, ending the operation of the pump.

Aspect 10. The method according to aspect 9, according to a second mode:
- if the volume removed from the tracked container is less than the second percentage of the target volume from the tracked container and if the air sensor detects air in the line, prompting the user for an input, and continuing operation of the pump after an air purge if a first input is received or ending the operation of the pump if a second input is received; and
- if the volume removed from the tracked container is more than the second percentage of the target volume from the tracked container and if the air sensor detects air in the line, ending the operation of the pump.

Aspect 11. The method according to aspect 10, wherein selection of the first mode or the second mode is based on an untracked infusion from the tracked container.

Aspect 12. The method according to any one of aspects 9-11, wherein the first percentage is 50% and the second percentage is 95%.

Aspect 13. The method according to any one of aspects 9-12, wherein the pump is a rotary peristaltic pump, and the monitoring of the operation of the pump comprises tracking revolutions of the pump.

Aspect 14. The method according to any one of aspects 9-13, further comprising:
- selectively operating a separator having an input port, a first output port, and a second output port, the separator configured to separate a biological fluid that enters at the input port into a first component that exists at the first output port and a second component that exists at the second output port; and selectively operating the pump to deliver biological fluid to the separator and to draw fluid from the tracked container.

Aspect 15. The system according to aspect 14, further comprising:
- monitoring a scale to receive a first component container, the first component container in fluid communication with the first output port to determine when a target volume of the first component is received in the first component container;
- operating the pump to deliver to the biological fluid to the separator and operating the separator until the target volume is received in the first component container; and
- operating the pump to deliver fluid from the tracked container.

The invention claimed is:

1. A system for processing a biological fluid with container volume tracking, comprising:
   - a pump configured to receive a line connected to a tracked container;
   - an air sensor associated with the line and configured to detect if air is in the line;
   - an output display configured to display prompts to a user;
   - an input device to receive inputs from the user; and
   - a controller coupled to the pump, the air sensor, the output display, and the input device, the controller configured to operate in a first mode and a second mode wherein said operation in said first mode is based on no prior infusion from said tracked container during biological fluid processing and wherein said second mode is based on an untracked prior infusion from said tracked container during biological fluid processing and is further configured to:

monitor operation of the pump;
determine a volume removed from the tracked container based on the
operation of the pump; and
according to the first mode:
  if the volume removed from the tracked container is less than a first percentage of a target volume from the tracked container and if the air sensor detects air in the line, continue operation of the pump after an air purge;
  if the volume removed from the tracked container is more than the first percentage of the target volume from the tracked container and less than a second percentage of the target volume from the tracked container and if the air sensor detects air in the line, prompt the user for an input, and continue operation of the pump after an air purge if a first input is received or end the operation of the pump if a second input is received; and
  if the volume removed from the tracked container is more than the second percentage of the target volume from the tracked container and if the air sensor detects air in the line, end the operation of the pump.

2. The system according to claim 1, wherein the controller is configured to, according to the second mode:
  if the volume removed from the tracked container is less than the second percentage of the target volume from the tracked container and if the air sensor detects air in the line, prompt the user for an input, and continue operation of the pump after an air purge if a first input is received; and
  if the volume removed from the tracked container is more than the second percentage of the target volume from the tracked container and if the air sensor detects air in the line, end the operation of the pump.

3. The system according to claim 1, wherein the first percentage is 50% and the second percentage is 95%.

4. The system according to claim 1, wherein the pump is a rotary peristaltic pump, and the controller is configured to monitor the operation of the pump by tracking revolutions of the pump.

5. The system according to claim 1 further comprising: a separator having an input port, a first output port, and a second output port, the separator configured to separate a biological fluid that enters at the input port into a first component that exists at the first output port and a second component that exits at the second output port,
  the controller coupled to the separator, the controller configured to selectively operate the separator and to selectively operate the pump to deliver biological fluid to the separator and to draw fluid from the tracked container.

6. The system according to claim 5, further comprising:
  a scale to receive a first component container, the first component container in fluid communication with the first output port,
  the controller coupled to the scale, the controller configured to monitor the scale to determine when a target volume of the first component is received in the first component container, to operate the pump to deliver to the biological fluid to the separator and to operate the separator until the target volume is received in the first component container, and to operate the pump to deliver fluid from the tracked container after the target volume is received in the first component container.

7. The system according to claim 1, wherein the separator comprises a spinning membrane.

8. The system of claim 1 wherein said tracked container comprises a volume of saline.

* * * * *